United States Patent
Hayakawa

(10) Patent No.: US 8,293,222 B2
(45) Date of Patent: Oct. 23, 2012

(54) SILICONE-MODIFIED WAX-CONTAINING COMPOSITION AND COSMETIC PREPARATION CONTAINING THE COMPOSITION

(75) Inventor: Chihiro Hayakawa, Yokohama (JP)

(73) Assignee: Shin-Etsu Chemical Co., Ltd., Tokyo (JP)

( * ) Notice: Subject to any disclaimer, the term of this patent is extended or adjusted under 35 U.S.C. 154(b) by 310 days.

(21) Appl. No.: 12/696,765

(22) Filed: Jan. 29, 2010

(65) Prior Publication Data

US 2011/0028571 A1   Feb. 3, 2011

(30) Foreign Application Priority Data

Jul. 28, 2009   (JP) .................. 2009-175185

(51) Int. Cl.
*A61K 31/74* (2006.01)
*A61K 9/00* (2006.01)
*A61K 8/02* (2006.01)

(52) U.S. Cl. ............ 424/78.08; 424/400; 424/401

(58) Field of Classification Search .............. None
See application file for complete search history.

(56) References Cited

U.S. PATENT DOCUMENTS

| | | | | |
|---|---|---|---|---|
| 5,412,004 A * | 5/1995 | Tachibana et al. | .............. | 524/27 |
| 5,897,869 A * | 4/1999 | Roulier et al. | .............. | 424/401 |
| 6,180,123 B1 * | 1/2001 | Mondet | .......................... | 424/401 |
| 7,943,120 B2 * | 5/2011 | Toyoda et al. | .............. | 424/70.12 |
| 2003/0082218 A1 * | 5/2003 | Ichinohe et al. | .............. | 424/401 |
| 2004/0071741 A1 * | 4/2004 | Derian | .......................... | 424/400 |
| 2006/0128882 A1 * | 6/2006 | Ichinohe | .......................... | 524/588 |
| 2006/0140894 A1 * | 6/2006 | Toyoda et al. | .............. | 424/70.12 |
| 2007/0172505 A1 * | 7/2007 | Mougin et al. | .............. | 424/401 |
| 2008/0003195 A1 * | 1/2008 | Arnaud et al. | .............. | 424/78.03 |
| 2009/0081151 A1 * | 3/2009 | Toyoda et al. | .............. | 424/78.02 |
| 2009/0238781 A1 * | 9/2009 | Sakuta et al. | .............. | 424/59 |
| 2009/0252774 A1 * | 10/2009 | Kamei et al. | .............. | 424/401 |
| 2011/0027213 A1 * | 2/2011 | Kamei et al. | .............. | 424/78.03 |
| 2011/0117146 A1 * | 5/2011 | Inokuchi et al. | .............. | 424/401 |

FOREIGN PATENT DOCUMENTS

| | | |
|---|---|---|
| EP | 0 357 037 A2 | 3/1990 |
| JP | 2-132141 A | 5/1990 |
| JP | 2008-174571 A | 7/2008 |

* cited by examiner

*Primary Examiner* — Robert A Wax
*Assistant Examiner* — Olga V Tcherkasskaya
(74) *Attorney, Agent, or Firm* — Birch, Stewart, Kolasch & Birch, LLP

(57) ABSTRACT

A composition for cosmetic preparation and a cosmetic preparation including the composition are provided. The composition includes a silicone-modified wax having a melting point of 100° C. or above and an unctuous agent having a melting point of 80° C. or below. The composition is prepared by cooling after dissolving and mixing the silicone-modified wax and the unctuous agent at temperature equal to or higher than the melting point of the silicone-modified wax. The composition has a smooth feel and a glossy surface and can be blended in a cosmetic preparation without being heated at 100° C. or above.

22 Claims, No Drawings

SILICONE-MODIFIED WAX-CONTAINING COMPOSITION AND COSMETIC PREPARATION CONTAINING THE COMPOSITION

BACKGROUND OF THE INVENTION

1. Field of the Invention

The present invention relates to a silicone-modified wax-containing composition and a cosmetic preparation containing the composition. The composition is suitably in a past or slurry form at room temperature and can be blended in the cosmetic preparation without being melted at high temperatures.

2. Description of the Related Art

An oily thickening agent such as a wax or a gelling agent (hereinafter collectively referred to as the "thickening agent") is used for the purpose of increasing a viscosity of oily components in a cosmetic preparation to improve a usability, a stability and an appearance of the cosmetic preparation. Here, the wax indicates broadly solid unctuous agents at room temperature. As the oily thickening agent, hydrocarbon-based waxes such as ceresin, polyethylene and ozokerite, natural waxes (i.e., wax esters) such as carnauba wax and candelilla wax, and polysaccharide fatty acid esters such as sucrose palmitic acid ester have been widely utilized.

These thickening agents are usually necessary to be melted at a temperature equal to or higher than a melting point of the thickening agent when blended in the cosmetic preparation. Therefore, when a thickening agent having a high melting point is blended, other components in the cosmetic preparation may be deteriorated or decomposed. Thus, it is desired that the melting point is low and particularly lower than 100° C. However, a thickening agent having a low melting point generally has a low thickening effect, and decrease in the viscosity or a phase separation of the cosmetic preparation may occur in some cases in a summer season. From these points, the melting point of a thickening agent is preferably about 60 to 95° C.

It is also desired that the thickening agent has a good compatibility with a low-viscosity unctuous agent that is blended in the cosmetic preparation. If the compatibility is poor, the thickening agent is separated from the unctuous agent with time, or crystals of the thickening agent become large when the cosmetic preparation is cooled, to impair the appearance and a feel of the cosmetic preparation in some cases. Further, it is desired that the thickening agent matches with other thickening agents well. If they do not match well, one thickening agent may inhibit the thickening effect of other thickening agents.

A silicone oil has been frequently used as an unctuous agent for cosmetic preparations because it has excellent properties, e.g., it has a non-viscous feel, its spread is good and its water-repellent property is good. Among them, a silicone oil having a low viscosity is frequently used for composing cosmetic preparations having a light feel and no greasy feeling. However, the silicone oil has a poor compatibility with common unctuous agents, does not match with thickening agents, and easily causes the above problems. The silicone oil also has the problem that the silicone oil has a good flatting property, excessively spreads when applied on the skin and thus can not form a cosmetic film having a thickness which gives a fatted adhesive feeling.

In order to solve the above problems, thickening agents which can thicken the silicone oil having a low viscosity have been developed (Patent Documents 1 to 3). However, it is difficult for any of them to smoothly thicken the silicone oil alone, and a resulting thickened one lacks a smoothness required for cosmetic preparations. Thus, a silicone-modified olefin-based wax has been proposed for solving these problems (Patent Document 4)

Patent Document 1: EP 0357037 A2
Patent Document 2: US 2004/0071741 A1
Patent Document 3: JP 2-132141 A
Patent Document 4: JP 2008-174571 A

SUMMARY OF THE INVENTION

When the above silicone-modified olefin-based wax is blended in a cosmetic preparation, it is heated and dissolved together with an unctuous agent (e.g., Patent Document 4, Paragraph 0202). Although the temperature at which they are heated and dissolved is unknown, the temperature is typically equal to or higher than the melting point of the wax. Therefore, when a silicone having a melting point of 100° C. or above among the silicones described in the above reference is blended, it is necessary to take measure so that the other components in the cosmetic preparation are not deteriorated. It is also described that the above silicone-modified olefin-based wax is heated and dissolved together with an unctuous agent, subsequently they are cooled to room temperature, and then a silicone-based composition which is solidified at room temperature and has no fluidity is obtained and this composition can be used as a cosmetic preparation (Patent Document 4, Paragraph 0195). However, this composition has room for improvement in terms of spreading property and feel.

Thus, it is an object of the present invention to provide a silicone-modified wax composition which is unnecessary to be heated at 100° C. or above in producing cosmetic preparations, exhibits an excellent feel and can further be combined with other thickening agents, and a cosmetic preparation containing the composition.

As a result of an extensive study for solving these problems, the present inventor has found that the above problems can be resolved by a composition which is suitably in a paste or slurry form at room temperature and is prepared by cooling with stirring after heating, dissolving and mixing a silicone-modified olefin wax together with an unctuous agent. That is, the present invention provides a composition for cosmetic preparations, comprising a silicone-modified wax having a melting point of 100° C. or above and an unctuous agent having a melting point of 80° C. or below, wherein the composition is prepared by cooling (typically to room temperature) after dissolving and mixing the silicone-modified wax together with the unctuous agent at a temperature equal to or higher than the melting point of the silicone-modified wax and is suitably in a paste or slurry form at room temperature.

Also, the present invention provides a method of preparing a composition for cosmetic preparations comprising 1) a step of dissolving and mixing a silicone-modified wax having a melting point of 100° C. or above and an unctuous agent having a melting point of 80° C. or below at a temperature equal to or higher than the melting point of the silicone-modified wax; and 2) a step of cooling the mixture obtained in the step 1) with stirring.

The composition of the present invention has a smooth feel and a glossy surface and can be blended in a cosmetic preparation without being heated at 100° C. or above. Further, the composition of the present invention can be combined with other thickening agents such as carnauba wax and can form a velvety cosmetic film.

DETAILED DESCRIPTION OF THE PREFERRED EMBODIMENTS

In the silicone-modified wax composition (hereinafter sometimes referred to as a "silicone wax composition" simply) of the present invention, the silicone-modified olefin-based wax described in above Patent Document 4 can be used as the silicone-modified wax. This wax is obtained by an addition reaction of an organohydrogenpolysiloxane with an olefin-based wax which is a copolymer of ethylene and at least one diene or a copolymer obtained by copolymerizing ethylene, at least one olefin selected from α-olefins having 3 to 12 carbon atoms and at least one diene. The organohydrogenpolysiloxane has at least one hydrosilyl group per one molecule, preferably in its side chain.

Among them, a silicone-modified olefin wax with high purity obtained by adding an organohydrogenpolysiloxane to a copolymer obtained by copolymerizing ethylene, at least one olefin selected from α-olefins having 3 to 12 carbon atoms and vinyl norbornene is preferred. In particular, butylpolydimethylsiloxyl (ethylene/propylene/vinyl norbornene) copolymer is preferred and this copolymer is described in THE INTERNATIONAL COSMETIC INGREDIENT DICTIONARY AND HANDBOOK, 12th EDITION. This has good compatibility with silicone oils such as dimethylpolysiloxane and an unctuous agent, such as trioctanoin and squalane, utilized for cosmetics, and can form stable compositions.

The melting point of the silicone wax is not particularly limited as long as it is 100° C. or above, and the silicone wax having a melting point of typically 100 to 140° C. and particularly 100 to 130° C. can be used suitably.

In the silicone wax composition, the unctuous agent is an unctuous agent which has been widely used for cosmetic preparations, has a melting point of 80° C. or below, preferably 30° C. or below, and is liquid, semi-solid or solid at room temperature. Since the composition contains such an unctuous agent, when the composition is applied to a skin and then liquefies, it gives a unique feel, and when the composition is blended in a cosmetic preparation, it can be handled like a liquid oil. The unctuous agent includes, for example, hydrocarbon oils, higher fatty acids, higher alcohols, ester oils, animal and plant oils, fluorine-containing oils and silicone oils. The "room temperature" herein means a temperature of 25±5° C.

The hydrocarbon oils include ozokerite, α-olefin oligomers, paraffin, isoparaffin, isododecane, squalane, ceresin, paraffin waxes, polyethylene waxes, polyisobutylene, hydrogenated polyisobutene, microcrystalline waxes and petrolatum. Volatile hydrocarbon oils at room temperature among the hydrocarbon oils form a coating film on a skin after being volatilized and give a refreshing feel. Non-volatile liquid oils are used for improving feel and gloss, and solid oils are used for thickening other unctuous agents.

The higher fatty acids may be straight, branched, saturated or unsaturated, and include, for example, lauric acid, myristic acid, palmitic acid, stearic acid, behenic acid, oleic acid, isostearic acid and 12-hydroxystearic acid. These are used for the purpose of stabilizing the cosmetic preparation, as an emulsifier, an aid for emulsification, a thickening agent for oils or the like. In particular, isostearic acid which is a branched fatty acid is useful as an aid for emulsification.

The higher alcohols include myristyl alcohol, palmityl alcohol, stearyl alcohol, behenyl alcohol, oleyl alcohol, isostearyl alcohol, hexyldodecanol, octyldodecanol, cetyl alcohol, cholesterol, phytosterol, batyl alcohol and selachyl alcohol. These are useful as an aid for emulsification.

The ester oils include monoesters such as cetyl 2-ethylhexanoate, isononyl isononanoate, 2-ethylhexyl isononanoate isotridecylpalmitate, octyldodecyl myristate, neopentyl glycol dioctanoate and neopentyl glycol dicaprate; dibasic acid ester such as diisopropyl sebacate and diisostearyl malate; triglyceride such as triethylhexanoin; polyglycerine ester such as polyglyceryl-2 triisostearate; trimethylolpropane derivatives such as trimethylolpropane triisostearate and trimethylolpropane tri-2-ethylhexanoate; phytosterol ester such as phytosteryl 12-hydroxystearate and phytosteryl isostearate; amino acid-based ester such as N-lauroyl-L-glutamate-2-octyldodecyl; and pentaerythritol ester of fatty acid such as hydroxystearic acid and rosin acid such as (hydroxystearate, stearate, rosin acid) dipentaerythritol. These exhibit effects of controlling feel, making components compatible, enhancing dispersibility of pigments, enhancing gloss and enhancing emollient and moisturizing property.

The animal and plant oils include animal and plant oils obtained by refining an avocado oil, a linseed oil, an almond oil, an olive oil, ibota wax, a cacao butter, a carnauba wax, a candelilla wax, a wheat germ oil, a sesame oil, a rice germ oil, a rice bran oil, a safflower oil, a shea butter, a jojoba oil, squalane, a soybean oil, a camellia oil, an evening primrose oil, a corn oil, a rape oil, a rice bran wax, a palm nucleus oil, a castor oil, a sunflower oil, a macadamia nut oil, a bee wax, a meadowfoam oil, a cotton seed oil, a Japan wax, a montan wax, a peanut oil, lanolin, liquid lanolin and an egg yolk oil. Hydrogenated ones thereof include the jojoba oil, a cured castor oil, a cured rape oil and reduced lanolin.

The fluorine-containing oils include perfluoropolyoxyalkylene, perfluorodecalin and perfluorooctane.

The silicone oils include straight-chain silicone oils such as dimethylpolysiloxane, caprylyl methicone, cetyl dimethicone, phenyl trimethicone, methyl trimethicone, diphenylsiloxyphenyl trimethicone, methylphenylpolysiloxane and methylhexylpolysiloxane; cyclic organopolysiloxanes such as octamethylcyclotetrasiloxane, decamethylcyclopentanesiloxane (hereinafter referred to as "D5"), dodecamethylcyclohexanesiloxane and tetramethyltetraphenylcyclotetrasiloxane; branched organopolysiloxanes such as tristrimethylsiloxymethylsilane and tetraxistrimethylsiloxysilane; amino-modified organopolysiloxanes, silicone gums such as gum-form dimethylpolysiloxanes having a high polymerization degree, gum-form amino-modified organopolysiloxanes and gum-form copolymers of a dimethylsiloxane and a methylpheylsiloxane; as well as higher fatty acid-modified organopolysiloxanes, alkyl-modified organopolysiloxanes, long chain alkyl-modified organopolysiloxanes, amino-modified organopolysiloxanes, and fluorine-modified organopolysiloxanes.

Preferably, an unctuous agent which is liquid at room temperature is used. For example, a hydrocarbon oil such as squalane, isododecane and isoparaffin; an ester oil having a branched structure, such as triethylhexanoin, neopentyl glycol diethylhexanoate and isotridecyl isononanoate; and a silicone oil are preferred, and more preferably an silicone oil is used. The composition containing the silicone oil can give a cosmetic preparation with less greasiness but with a smooth feel. Among the silicone oils, dimethylpolysiloxane is preferred, and in particular dimethylsiloxane and derivatives thereof having a viscosity of 2 to 10 mm$^2$/s at room temperature are preferred.

In the silicone wax composition, a content of the silicone-modified wax is preferably 5 to 60% by mass and more preferably 10 to 40% by mass, and a content of the unctuous agent is preferably 40 to 95% by mass and more preferably 60 to 90% by mass based on a total mass of the composition.

When the content of the silicone-modified wax is less than the above lower limit, a sufficient thickening effect may not achieved when blended in a cosmetic preparation. Meanwhile, when it exceeds the above upper limit, the feel of the composition is bad and it may be necessary to heat at 100° C. or above when blended in a cosmetic preparation.

The silicone wax composition is in a solid form, paste form (semi-solid form) or slurry form at room temperature, and is suitably in a paste or slurry form. The slurry indicates a state in which fine solid wax fine particles are suspended in a liquid unctuous agent, and exhibits (self)fluidity at room temperature. The paste also indicates a state in which fine solid wax fine particles are suspended in a liquid unctuous agent, and exhibits no fluidity or scarcely exhibits (self)fluidity without any force being added, but when a certain force is added, the fluidity of the paste is increased. The composition has a smooth feel, and can become a cosmetic preparation by itself. The composition also has an excellent thickening effect and can compose a cosmetic preparation with a smooth feel.

The silicone wax composition can be made by a method, comprising the following steps:
1) a step of dissolving and mixing a silicone-modified wax having a melting point of 100° C. or above and an unctuous agent having a melting point of 80° C. or below at a temperature equal to or higher than the melting point of the silicone-modified wax; and
2) a step of cooling the mixture obtained in the step 1) with stirring.

A solidified product obtained when the mixture is spontaneously cooled without being stirred has a bad feel. When the solidified product obtained when the mixture is spontaneously cooled is blended in a cosmetic preparation, the blending is sometimes difficult unless the materials are heated to a temperature equal to or higher than the melting point of the silicone-modified wax.

As a stirring procedure, publicly known procedures such as a disper, a paddle mixer and a rubber scraper can be used. Cooling may be spontaneous cooling or cooling with water.

When a silicone wax composition obtained through the above steps 1) and 2) is blended in a cosmetic preparation, it is unnecessary to melt the silicone-modified wax itself dispersed in the composition, and the composition can be mixed with heating at a temperature lower than 100° C. or without heating.

The present invention also relates to a cosmetic preparation containing the silicone wax composition. The cosmetic preparation can be made by a method comprising the following step:
3) a step of mixing the silicone-modified wax composition for a cosmetic preparation, which has been prepared by the preparation method comprising the above steps 1) and 2) with at least one of other components to be blended in the cosmetic preparation at a temperature lower than 100° C.

The silicone wax composition obtained by the steps 1) and 2) is suitably used particularly as a thickening component for an oily cosmetic preparation. As other components to be blended in the cosmetic preparation, components typically used for cosmetics, e.g., an unctuous agent, a powder component, a surfactant, a thickening agent, a film former, an ultraviolet light absorber, a drug and the like can be used. Their amounts to be blended may be amounts within ranges in which the effects of the present invention are not impaired.

The unctuous agent may be an unctuous agent usually used for cosmetic preparations, and also includes the aforementioned unctuous agent as the unctuous agent for preparing the silicone wax composition. This unctuous agent may be the same as or different from the unctuous agent contained in the silicone wax composition. Preferably, hydrocarbon oils, ester oils or silicone oils are used.

Viscosity which is characteristic of an oily cosmetic preparation can be controlled by using the silicone wax composition and at least one wax selected from the hydrocarbon waxes and natural waxes in combination as an unctuous agent which is solid at room temperature. That is, the cosmetic preparation which enables an application with no greasiness but with a thickness can be prepared. In this case, preferably, the method further comprises a step 4) of cooling the mixture obtained in the step 3) with stirring after the step 3).

The hydrocarbon wax is a wax composed mainly of a hydrocarbon, and includes for example, ceresin, a polyethylene wax, a microcrystalline wax, a paraffin wax, ozokerite, and a synthesized hydrocarbon wax. The natural wax is a wax originating from animals or plants and composed mainly of ester of a higher alcohol and a higher fatty acid, and includes, for example, a carnauba wax, a candelilla wax, a rice wax, a bee wax and a hydrogenated jojoba oil. Among them, those having a melting point of 60 to 95° C. are particularly preferred, and ceresin and the carnauba wax are preferred. A cosmetic preparation in various forms, e.g., a cosmetic preparation filled in a tube or a jar container can be prepared by mixing the silicone wax composition with the wax at a temperature lower than 100° C. in the step 3) and then cooling with stirring in the same way as in the step 2) (step 4)). A preferable mix ratio (mass ratio) of the silicone wax composition to the wax may be in a range of from 5:95 to 91:9. When the silicone wax composition is mixed with the wax, the unctuous agent may be added. This unctuous agent may be the same as or different from the unctuous agent contained in the silicone wax composition. In that case, the preferable mix ratio (mass ratio) of silicone wax composition and the wax to the unctuous agent, i.e., the ratio of (silicone wax composition+wax):unctuous agent (mass ratio) is in a range of from 4:96 to 40:60.

As the powder component in the cosmetic preparation, any powders which have been conventionally used for cosmetic preparations can be used regardless of the shape of the particles (spherical, needle, platy, dendritic, fibrous or irregular shape), particle diameter and particle structure (porous, non-porous, hollow or hollow porous structure). Such powders include inorganic powders, organic powders, metal soaps and powders for coloring. These powder components may have been surface-treated with a metal soap, silica, oxidized aluminum, aluminum hydroxide or other methods known publicly, or may be composite powders, for the purpose of suppressing a surface activity, enhancing dispersibility and improving feel when the cosmetic preparation is applied.

Examples of the inorganic powder include ultraviolet light absorption scattering agents such as fine particle titanium oxide, fine particle zinc oxide and fine particle cerium oxide, and extender pigments such as barium sulfate, calcium carbonate, magnesium carbonate, talc, mica, kaolin, sericite, synthesized gold mica, silica, hydroxyapatite and boron nitride. A dispersion in which the above ultraviolet light absorption scattering agent has been previously dispersed in the unctuous agent can also be used. Commercially available products thereof include SPD-T5 and SPD-Z5 supplied from Shin-Etsu Chemical Co., Ltd.

Examples of the organic powders include polyester powders, polyethylene powders, polystyrene powders, polyurethane powders, polymethyl methacrylate powders, methyl methacrylate crosspolymers, cellulose powders, silk powders, powders of nylon such as 12 nylon and 6 nylon, fibrous powders thereof, crosslinked silicone fine powders having a structure of crosslinked dimethylpolysiloxane, crosslinked polymethyl silsesquioxane fine powders, fine powders obtained by coating the surface of a crosslinked organopolysiloxane rubber with polymethyl silsesquioxane particles, laminated powders of a resin, starch powders, fatty acid starch derivative powders and lauroyl lysine.

In particular, a non-viscous, soft and excellent feel as well as a good dispersibility can be given to the cosmetic preparation by using a powder obtained by coating the surface of a crosslinked organopolysiloxane rubber such as (vinyl dimethicone/methicone silsesquioxane) crosspolymer or (diphenyl dimethicone/vinyldiphenyl dimethicone/silsesquioxane) crosspolymer with polymethyl silsesquioxane particles as a part of the powder. Commercially available products thereof include KSP-100, KSP-101, KSP-102, KSP-105 and KSP-300 supplied from Shin-Etsu Chemical Co., Ltd.

The metal soap includes zinc stearate and aluminum stearate.

As the powder for coloring, inorganic coloring pigments such as titanium oxide, iron oxide, titanium black, carbon black, chromium hydoxide, chromium oxide, Prussian blue, ultramarine blue and aluminum powders, tar dyestuffs such as red No. 262 and yellow No. 4, natural dyestuffs such as carmine, and pearl pigments such as mica titanium, iron oxide-coating mica titanium and titanium oxide-coating synthesized gold mica are available.

These powders can be surface-treated with one or more commercially available film formers and surface treating agents if necessary to an extent in which the effects of the present invention are not impaired. As the surface treating agent, for example, KF-9908, KF-9909 and KP-574 (supplied from Shin-Etsu Chemical Co., Ltd.) exhibit excellent dispersibility depending on its purpose.

The surfactant among the components of the cosmetic preparation is not particularly limited as long as it has been conventionally used for cosmetic preparations, and any surfactants can be used. As such a surfactant, anionic, cationic, nonionic and ampholytic surfactants are available.

As the anionic surfactants, for example, fatty acid soaps such as sodium stearate are known as an emulsifier of an O/W type, and branched fatty acid soaps such as sodium isostearate are in some cases used for enhancing the stability of a W/O type emulsion. The ampholytic surfactants include betaine, phosphatidyl choline, aminocarboxylate salts, imidazoline derivatives and amide amine types.

As the nonionic surfactants, substances having a hydrocarbon-based activator as a hydrophobic group, e.g., sorbitan fatty acid ester, glycerine fatty acid ester, polyglycerine fatty acid ester, propylene glycol fatty acid ester, sucrose fatty acid ester, methyl glycoside fatty acid ester, alkyl polyglycoside, polyoxyalkylene fatty acid ester and polyoxyethylene cured castor oil, and substances having a silicone-based activator as a hydrophobic group, e.g., polyoxyalkylene-modified organopolysiloxane are known well.

Among these surfactants, the silicone-based surfactant is useful as a W/O type surfactant. As commercially available products of the silicone-based surfactant, KF-6017 (supplied from Shin-Etsu Chemical Co., Ltd.) is available. Among them, a silicone-based surfactant which is a branched organopolysiloxane having a polyoxyethylene chain or a polyglycerine chain in its molecule is useful as a silicone-containing surfactant of the W/O type. Further, a surfactant having an alkyl branch on the silicone skeleton is well compatible with other cosmetic unctuous agent and enables to select an unctuous agent broadly. As commercially available products thereof, KF-6028, KF-6028P, KF-6038, KF-6100, KF-6104 and KF-6105 (supplied from Shin-Etsu Chemical Co., Ltd.) are available. The aforementioned surfactant having a polyglycerine chain is also known to be excellent in dispersibility of pigments. The hydrocarbon-based surfactant is utilized in O/W type emulsification, and is known to be also used in combination with the above silicone-based surfactant in the W/O type emulsification. For example, a hydrophilic polyoxyalkylene fatty acid ester, sorbitan sesquioleate and sorbitan sesquiisostearate are combined for enhancing the dispersion of pigments and the stability of emulsification.

The thickening agent among the components of the cosmetic preparation is not particularly limited as long as it has been conventionally used for cosmetics. Such thickening agents are classified into an aqueous type and an oily type.

As the aqueous type thickening agent, fine particle silica; inorganic powders such as bentonite and hectorite; water-soluble polymers, e.g., gum arabic, guar gum, carrageenan, agar, quince seed, locust bean gum, xanthan gum, pullulan, carboxymethylcellulose sodium, hydroxyethylcellulose, vinyl-based polymers such as carboxyvinyl polymers, acryl-based polymers such as (acryloyldimethyl taurine ammonium/VP) copolymers, (sodium acrylate/sodium acryloyldimethyl taurine) copolymers, (hydroxyethyl acrylate/sodium acryloyldimethyl taurine) copolymers and polyacrylamide can be used. By using the above acryl-based polymer, it is possible to stabilize the emulsification of the O/W type relatively easily.

The oily type thickening agent includes hydrophobilized fine particle silicas such as silylated silica, organic modified clay minerals such as disteardimonium hectorite, metal soaps such as aluminum stearate, polysaccharide fatty acid esters such as dextrin (palmitate/2-ethylhexanoate) and inulin stearate, sucrose fatty acid esters such as acetate stearate sucrose, and crosslinked organopolysiloxanes.

The hydrophobilized fine particle silica even in a small amount can absorb oily components in a large amount, the organic modified clay mineral enhances the stability of emulsification by being combined with a surfactant and can thicken a cosmetic preparation by addition of a polar additive such as propylene carbonate, and further dextrin (palmitate/2-ethylhexanoate) can form a thickened gel with suppressed syneresis. Thus, they are useful for thickening or stabilizing an oily or W/O type cosmetic preparation.

As the crosslinked organopolysiloxane is preferred one which swells by including a liquid oil in an amount equal to or more than its own weight, and may contain at least one moiety selected from the group consisting of a polyoxyalkylene moiety, a polyglycerine moiety, an alkyl moiety, an alkenyl moiety, an aryl moiety and a fluoroalkyl moiety in its molecule. As commercially available products thereof, KSG series (supplied from Shin-Etsu Chemical Co., Ltd.) made into the paste form with the unctuous agent is available. These crosslinked type organopolysiloxane has a non-viscous feel with less greasiness and is excellent in thickening and stabilization of oily or W/O type cosmetic preparations.

As the film former among the components of the cosmetic preparation, any film formers which have been used conventionally for cosmetic preparations can be used without particular limitation. Such film formers can be classified into an aqueous type and an oily type. As the aqueous type film former, emulsions of polyvinyl alcohol, polyvinyl pyrrolidone, a copolymer of vinyl acetate and vinyl pyrrolidone and an acrylic acid-based copolymer can be used.

The oily type film formers includes α-olefin/vinyl pyrrolidone copolymers such as eicosene/vinyl pyrrolidone copolymers, acrylic acid/alkyl acrylate copolymers, silicone net resins of trimethylsiloxysilic acid, acryl silicone resins of acryl/silicone grafts or block copolymers of (alkyl acrylate/ dimethicone) polymers. Further, as the acryl silicone resin and the silicone net resin, those containing a pyrrolidone moiety, a long chain alkyl moiety, a polyoxyalkylene moiety, and fluoroalkyl moiety, and an anion moiety such as carboxylic acid in their molecule can also be used. The commercially available products of these film formers include KP-543, KP-545 and KP-550 (supplied from Shin-Etsu Chemical Co., Ltd.).

The ultraviolet light absorber among the components of the cosmetic preparation is not particularly limited as long as it has been conventionally used for cosmetic preparations. Such an ultraviolet light absorber includes, for example, polysilicone-15, octocrylene, ethylhexyl methoxycinnamate, t-butylmethoxydibenzoylmethane, methylenebisbenzotriazolyl tetramethylbutylphenol, octyl salicylate, homosalate, phenylbenzimidazole sulfonic acid, hydroxymethoxybenzophenone sulfonic acid, and dimethyl-PABA-octyl (2-ethylhexyl paradimethylaminobenzoic acid).

The drug among the components of the cosmetic preparation includes, for example, antiperspirants such as aluminum chlorohydrate; antioxidants such as tocopherol; amino acids and derivatives thereof such as glycine, serine, arginine and glutamine; nicotinic acid compounds and other vitamins and derivatives thereof, e.g., vitamins A such as vitamin A oil and retinol, vitamins B such as pyridoxine hydrochloride salts, panthenol, panthotenylethyl ether, nicotinic acid amide and cynanocobalamine, vitamins C such as palmitate ascorbate and glucoside ascorbate, vitamins E such as $\alpha$-tocopherol; and anti-inflammatory agents such as glycyrrhizinate K2 salts.

The silicone wax composition of the present invention can be blended in various cosmetic preparations such as skin care products, makeup products, hair products, antiperspirant products and ultraviolet light protecting products. The form of the cosmetic preparation is not limited and may be a solid, a powder, a liquid, an emulsion such as a water-in-oil type emulsion, an oil-in-water type emulsion and a non-aqueous emulsion. Cosmetic preparation products include, for example, skin lotions, milk lotions, creams, cleansing creams, packs, massage preparations, beauty solutions, beauty oils, washing agents, hand creams, lip creams, wrinkle masking cosmetic preparations, makeup foundations, concealers, white powders, powder foundations, liquid foundations, cream foundations, oily foundations, cheek rouges, eye shadow, eyelash liners, eye liners, eyebrow pencils, lip rouges, manicure preparations, shampoos, rinses, treatments, hair set agents, antiperspirant cosmetic preparations, sun block milk lotions and sun block creams.

EXAMPLES

The present invention will be further described with reference to the following Examples, but the present invention is not limited thereto. Amounts to be blended in the following are based on % by mass unless otherwise indicated.

Preparation Example 1 of Silicone-Modified Wax Composition

A butyl polydimethylsiloxyl (ethylene/propylene/vinyl norbornene) copolymer (20%, melting point: 120° C.) as a silicone-modified wax and a dimethylpolysiloxane (80%, KF-96A-6cs supplied from Shin-Etsu Chemical Co., Ltd.) as an unctuous agent were weighed and placed in a beaker, heated at 140° C. and dissolved using an oil bath, and then gradually cooled to 25° C. with stirring using a rubber scraper so that the mixture became uniform to obtain a silicone-modified wax composition A.

Preparation Example 2 of Silicone-Modified Wax Composition

A silicone-modified wax composition B was obtained in the same way as in Preparation Example 1 of silicone-modified wax composition, except that the dimethylpolysiloxane as the unctuous agent was replaced with triethylhexanoin.

Preparation Example 3 of Silicone-Modified Wax Composition

A silicone-modified wax composition. C was obtained in the same way as in Preparation Example 1 of silicone-modified wax composition, except that the dimethylpolysiloxane as the unctuous agent was replaced with a plant-derived squalane.

Preparation Example 4 of Silicone-Modified Wax Composition

A silicone-modified wax composition D was obtained in the same way as in Preparation Example 1 of silicone-modified wax composition, except that the dimethylpolysiloxane as the unctuous agent was replaced with ceresin (Ceresin 810 supplied from Nikko Rica Corporation).

Preparation Example 5 of Silicone-Modified Wax Composition

A butyl polydimethylsiloxyl (ethylene/propylene/vinyl norbornene) copolymer (30%, melting point: about 120° C.) as a silicone-modified wax and a dimethylpolysiloxane (70%, KF-96A-6cs supplied from Shin-Etsu Chemical Co., Ltd.) as an unctuous agent were weighed and placed in a beaker, heated at 140° C. and dissolved using an oil bath, and then gradually cooled to 25° C. with stirring in the same way as in Preparation Example 1 to obtain a silicone-modified wax composition E.

Preparation Example 6 of Silicone-Modified Wax Composition

A silicone-modified wax composition F was obtained in the same way as in Preparation Example 1 of silicone-modified wax composition, except that the dimethylpolysiloxane as an unctuous agent was replaced with D5.

Comparative Preparation Example 1

Ceresin (20%, melting point: about 80° C.) and a dimethylpolysiloxane (80%, KF-96A-6cs supplied from Shin-Etsu Chemical Co., Ltd.) were mixed, heated, dissolved and cooled in the same way as in Example 1, and a liquid mixture G in which ceresin particles had been dispersed unevenly in the dimethylpolysiloxane was obtained. The mixture G had a rough touch. As described above, ceresin could not thicken the dimethylpolysiloxane.

Comparative Preparation Example 2

The preparation of a mixture was attempted in the same way as in Comparative Preparation Example 1, except that inulin stearate was used in place of ceresin, but the mixture was separated into two layers. It was confirmed that the wax and the gelling agent usually used could not thicken the dimethylpolysiloxane successfully.

<Nature and Behaviors of Silicone-Modified Wax Compositions A to F>

The resulting silicone-modified wax compositions A, B, C, D and F were uniform pastes with a low viscosity to a high viscosity, and the silicone-modified wax composition E was a uniform solid wax. When they were heated at 95° C., they became liquids with a low viscosity to a high viscosity (i.e., slurry or paste) in which silicone-modified wax particles (solid) in each composition had been dispersed in each unctuous agent (liquid oil). In this way, these compositions can be blended in a liquid form with a cosmetic preparation by heating at a temperature lower than 100° C. By cooling again with stirring, each composition was back to the original state of a paste with a low viscosity to a high viscosity or a solid.

<Storage Stability at 50° C.>

The silicone-modified wax composition A and the mixture G were stored in a thermostatic chamber at 50° C. for 3 hours, and cooled to 25° C. without being stirred. The mixture G lost its fluidity and became an uneven soft solidified one. It is assumed that the state of the wax in the mixture was changed due to temperature change. Meanwhile, no change was observed in the state of the silicone-modified wax composition A. It is assumed that the change of the state scarcely occurred because the silicone-modified wax had a high melting point. This could confirm that the composition A is excellent in stability in the storage at a high temperature of about 50° C.

Effect on Solidification of Liquid Oil by Ceresin: Preparation Examples (a) to (c)

Next, an effect of the silicone-modified wax composition on the solidification of an oil (liquid oil) by ceresin was confirmed by Preparation Examples (a) to (c) shown in Table 1. Amounts of components in the table are indicated in % by mass, and hardness in the table was measured using a rheometer supplied from Rheotec (attachment: 1φ bar).

TABLE 1

| Components | Preparation Example (a) | Preparation Example (b) | Preparation Example (c) |
|---|---|---|---|
| Silicone-modified wax composition A (Preparation Example 1) | — | 25 | — |
| Methylpolysiloxane (Note 4) | 50 | 25 | 45 |
| Dextrin Palmitate | — | — | 5 |
| Ceresin | 15 | 15 | 15 |
| Triethylhexanoin | 35 | 35 | 35 |
| Total (% by mass) | 100 | 100 | 100 |
| Hardness of obtained composition | 56 | 67 | 1 |

In each of Preparation Examples (a) to (c), the components in Table 1 were placed in a beaker, dissolved at about 90° C. using a hot water bath, and cooled by being left stand at 25° C. to prepare a mixture of the Preparation Examples.

As is seen when the hardness of the mixture of Preparation Example (b) is compared with that of Preparation Example (a), it was confirmed that the addition of the silicone-modified wax composition A did not prevent the effect of ceresin on the solidification of the oil (liquid oil). It was observed that the mixture of the Preparation Example (b) was more glossier than that of Preparation Example (a) on the surface.

The preparation Example (c) is one obtained by replacing 5% by mass of 50% by mass of methylpolysiloxane in Preparation Example (a) with dextrin palmitate known as an oily gelling agent. As shown by Preparation Example (c), if dextrin palmitate was added and combined with ceresin, the resulting composition was a liquid with a low viscosity.

Thus, it has been confirmed that dextrin palmitate prevents the solidification of the oil (liquid oil) by ceresin, but the contrary, that the silicone-modified wax composition A does not prevent the solidification of the oil (liquid oil) by ceresin differently from dextrin palmitate.

Preparation Examples (d) to (g) for Mixtures Containing a Wax or Natural Wax

Next, the thickening effect when a silicone-modified wax composition was combined with a hydrocarbon wax or a natural wax was confirmed by Preparation Examples (d) to (g) shown in Table 2. In each Example, components in Table 2 were placed in a beaker, dissolved at about 90° C. using a hot water bath, and cooled to 25° C. with stirring to prepare a mixture. Thus, respective mixtures of Preparation Examples (d) to (g) were obtained.

TABLE 2

| Components | Preparation Example (d) | Preparation Example (e) | Preparation Example (f) | Preparation Example (g) |
|---|---|---|---|---|
| Silicone-modified wax composition A (Preparation Example 1) | — | 25 | — | 25 |
| Methyl polysiloxane (Note 4) | 50 | 25 | 40 | 15 |
| Ceresin | 15 | 15 | — | — |
| Carnauba wax | — | — | 20 | 20 |
| Triethylhexanoin | 35 | 35 | 40 | 40 |
| Total (% by mass) | 100 | 100 | 100 | 100 |
| State of obtained composition | Low viscosity liquid | Paste form | High viscosity liquid | Paste form |

As is seen from comparison of Preparation Example (d) with Preparation Example (e), when the silicone-modified wax composition of the present invention is used, the mixture of methylpolysiloxane and triethylhexanoin can be thickened to produce a paste form. If carnauba wax is used, it is possible to thicken methylpolysiloxane (Preparation Example (f)). A paste composition can be made by blending a portion of methylpolysiloxane in a state in which the portion is contained in the silicone-modified wax composition and cooling with stirring (Preparation Example (g)). This paste composition had a good feel and could form a coating film having a thickness when applied on a skin. Meanwhile, the compositions of Preparation Examples (d) and (f) in which the silicone-modified wax composition had not been added were uneven and had a bad feel and appearance. A composition having the same formulation as in the Preparation Example (c) in which 5% by mass in 50% by mass of methylpolysiloxane in Preparation Example (d) had been replaced with dextrin palmitate known as an oily gelling agent was prepared by cooling to 25° C. with stirring, but a liquid with a low viscosity was obtained. From the results, it was found that any thickening effect was not obtained by combining the silicone-modified wax composition with dextrin palmitate.

Examples in which cosmetic preparations were prepared using the resulting silicone-modified wax compositions A to F are shown below. Unless otherwise indicated, heating in the following examples was performed at a temperature lower than 100° C. using a hot water bath.

Examples 1 to 2

Comparative Example 1

A W/O type emulsified cream was made with a formulation shown in Table 3.

TABLE 3

| | Components | Comparative Example 1 | Example 1 | Example 2 |
|---|---|---|---|---|
| 1 | Crosslinked polyether modified silicone (Note 1) | 3.0 | 3.0 | 3.0 |
| 2 | PEG-10 dimethicone (Note 2) | 0.3 | 0.3 | 0.3 |
| 3 | Crosslinked dimethyl polysiloxane (Note 3) | — | — | 4.0 |
| 4 | Methylpolysiloxane (Note 4) | 14.7 | 4.0 | — |
| 5 | Silicone-modified wax composition A (Preparation Example 1) | — | 10.7 | 10.7 |
| 6 | 1,3-Butylene glycol | 8.0 | 8.0 | 8.0 |
| 7 | Ethanol | 5.0 | 5.0 | 5.0 |
| 8 | Sodium citrate | 0.2 | 0.2 | 0.2 |
| 9 | Sodium chloride | 0.5 | 0.5 | 0.5 |
| 10 | Purified water | 68.3 | 68.3 | 68.3 |
| | Total (% by mass) | 100.0 | 100.0 | 100.0 |
| | Hardness (g) (Note 5) | 15 | 52 | 75 |

(Note 1)
KSG-210 (swollen methylpolysiloxane) supplied from Shin-Etsu Chemical Co., Ltd.
(Note 2)
KF-6017P supplied from Shin-Etsu Chemical Co., Ltd.
(Note 3)
KSG-15 (swollen D5) supplied from Shin-Etsu Chemical Co., Ltd.
(Note 4)
KF-96A-6cs supplied from Shin-Etsu Chemical Co., Ltd.
(Note 5)
Measured using a 20

(Production method) The components 1 to 5 were mixed, dispersed evenly, then to the resulting mixture a solution composed of the components 6 to 10 was added with stirring using a stirrer at high speed to obtain an objective W/O type emulsified cream. No heating was required in the method of preparing this cosmetic preparation.

As is evident by comparing Comparative Example 1 with Example 1, it has been found that the hardness (viscosity) of a W/O type emulsified cream was largely increased by replacing a part of methylpolysiloxane with the silicone-modified wax composition A to increase the viscosity of the oily phase in the cosmetic preparation. The crosslinked dimethylpolysiloxane is a gel of a silicone elastic body formed of a three dimensionally crosslinked dimethylpolysiloxane and swollen with silicone, and can be used for thickening silicone. It has been found from Example 2 that the combination therewith has no problem and further increases the hardness (viscosity). The stability with time and the temperature stability were good in the W/O type emulsified creams in Examples. The crosslinked dimethylpolysiloxane which is an elastic body and the silicone-modified wax composition A are largely different in their structures and also largely different in feel when the cosmetic preparations are applied. By combining these, it is possible to widely control the feel of cosmetic preparations.

Example 3

Treatment Cream

| Components | % by mass |
|---|---|
| 1. Crosslinked polyether-modified silicone (Note 1) | 4.0 |
| 2. Lauryl PEG-9 polydimethylsiloxyethyl dimethicone (Note 6) | 1.5 |
| 3. Alkyl-modified crosslinked dimethylpolysiloxane (Note 7) | 3.0 |
| 4. Jojoba oil | 6.0 |
| 5. Triethylhexanoin | 1.0 |
| 6. Silicone-modified wax composition A (Preparation Example 1) | 10.7 |
| 7. 1,3-Butylene glycol | 5.0 |
| 8. Glycerine | 3.0 |
| 9. Sodium citrate | 0.2 |
| 10. Sodium chloride | 0.5 |
| 11. Xanthan gum | Adequate quantity |
| 12. Purified water | 64.5 |
| 13. Preservative | Adequate quantity |

(Note 6)
KF-6038 supplied from Shin-Etsu Chemical Co., Ltd.
(Note 7)
KSG-43 (swollen triethylhexanoin) supplied from Shin-Etsu Chemical Co., Ltd.

(Production method) The components 1 to 6 were mixed to form a uniform dispersion, and then to the dispersion a uniform mixture of the components 7 to 13 separately prepared was added with stirring using a high speed stirrer to obtain an objective treatment cream.

The resulting treatment cream had no greasiness, spread well on hair and gave a fatted feel to the hair.

Example 4

Powder Foundation

| Components | % by mass |
|---|---|
| 1. Squalane | 1.0 |
| 2. Silicone-modified wax composition A (Preparation Example 1) | 6.0 |
| 3. Polyethylene powder | 1.5 |
| 4. Polymethyl silsesquioxane (Note 8) | 4.5 |
| 5. Phenyl-modified hybrid silicone complex (Note 9) | 3.0 |
| 6. Barium sulfate | 10.0 |
| 7. Hydrophobilized sericite (Note 10) | 40.0 |
| 8. Hydrophobilized talc (Note 10) | 23.2 |
| 9. Hydrophobilized coloring agent (Note 10) | 10.8 |

(Note 8)
KMP-590 supplied from Shin-Etsu Chemical Co., Ltd.
(Note 9)
KSP-300 supplied from Shin-Etsu Chemical Co., Ltd.
(Note 10)
Treated with KF-9909 supplied from Shin-Etsu Chemical Co., Ltd.

(Production method) The components 3 to 8 were pulverized to make a uniform mixture, the components 1 and 2 previously mixed at room temperature were added thereto to form a uniform dispersion, and then the dispersion was pressmolded in a mold to obtain a powder foundation. The resulting powder foundation had a non-viscous feel, spread well, made makeup last longer and was easily taken off.

Example 5

Solid W/O Foundation

| Components | % by mass |
|---|---|
| 1. Silicone-modified wax composition A (Preparation Example 1) | 11.5 |
| 2. Methylpolysiloxane (Note 4) | 2.0 |
| 3. Ceresin | 5.5 |
| 4. Neopentyl glycol dioctanoate | 8.0 |
| 5. Triethylhexanoin | 4.0 |
| 6. Crosslinked type polyglycerine-modified silicone (Note 11) | 4.0 |
| 7. Alkyl-modified branched polyglycerine-modified silicone (Note 12) | 1.5 |
| 8. Polymethyl silsesquioxane (Note 8) | 1.5 |
| 9. Hydrophobilized coloring agent (Note 10) | 10.0 |
| 10. Hydrogenated lecithin | 0.2 |
| 11. Polysorbate 80 | 0.3 |
| 12. Dipropylene glycol | 5.0 |
| 13. Preservative | Adequate quantity |
| 14. Purified water | 46.0 |

(Note 11)
KSG-710 (swollen methylpolysiloxane) supplied from Shin-Etsu Chemical Co., Ltd.
(Note 12)
KF-6105 supplied from Shin-Etsu Chemical Co., Ltd.

(Production method)
A: The components 1 to 8 were heated and dissolved to make a uniform mixture.
B: The components 9 to 13 were mixed, dispersed with a roller, added to the component 14, and they were heated and mixed.
C: While the mixture obtained in A was heated and stirred, the dispersion obtained in B was gradually added thereto to effect emulsification. The obtained emulsified mixture was poured in a stick-shaped mold or a compact-shaped mold to obtain a stick W/O foundation or a W/O compact foundation, respectively.

The resulting solid W/O foundation spread well and gave a fatted film feel with no greasiness to a skin.

Example 6

Creamy Rouge

| Components | % by mass |
|---|---|
| 1. Dextrin palmitate/ethylhexanoate (Note 13) | 9.0 |
| 2. Triethylhexanoin | 5.0 |
| 3. Acryl silicone dissolved in D5 (Note 14) | 8.0 |
| 4. Alkyl-modified crosslinked type dimethylpolysiloxane (Note 7) | 8.0 |
| 5. Alkyl-modified branched polyglycerine-modified silicone (Note 12) | 2.0 |
| 6. Decamethyl cyclopentasiloxane | 40.0 |
| 7. Silicone-modified wax composition C (Preparation Example 3) | 5.0 |
| 8. 1,3-Butylene glycol | 5.0 |
| 9. Purified water | 18.0 |
| 10. Coloring agent | Adequate quantity |
| 11. Mica | Adequate quantity |

(Note 13)
Rheopearl TT supplied from Chiba Flour Milling Co., Ltd.
(Note 14)
KP-545 (solid content 30%) supplied from Shin-Etsu Chemical Co., Ltd.

(Production method)
A: The component 10 was mixed with a part of the component 2, followed by dispersion using a roller mill, and the resulting dispersion was heated and mixed together with components 1 to 7.
B: The components 8 and 9 were heated, added to the mixture obtained in A, followed by emulsification and subsequent cooling.
C: The component 11 was added to the emulsified mixture obtained in B to obtain a creamy rouge.

The resulting creamy rouge spread lightly, had neither greasy nor oily feel and formed a film having a long life on lips

Example 7

Mascara

| Components | % by mass |
|---|---|
| 1. Branched polyether-modified silicone (Note 15) | 1.0 |
| 2. Dimethyl distearyl ammonium hectorite | 4.0 |
| 3. Isododecane | 28.2 |
| 4. Propylene carbonate | 1.3 |
| 5. Acryl silicone dissolved in D5 (Note 16) | 20.0 |
| 6. Dextrin palmitate/ethylhexanoate (Note 13) | 3.0 |
| 7. Ceresin | 2.5 |
| 8. Silicone-modified wax composition F (Preparation Example 6) | 10.0 |
| 9. Bee wax | 2.5 |
| 10. Triethylhexanoin | 3.0 |
| 11. Hydrogenated lecithin | 0.5 |
| 12. Silylated silica | 3.0 |
| 13. Hydrophobilized coloring agent (Note 10) | 10.0 |

(Note 15)
KF-6028P supplied from Shin-Etsu Chemical Co., Ltd.
(Note 16)
KP-550 (solid content 40%) supplied from Shin-Etsu Chemical Co., Ltd.

(Production method)
A: The components 1 to 3 were made into a uniform mixture, the component 4 was added thereto, followed by mixing.
B: The components 5 to 12 were heated, stirred and dissolved, the mixture obtained in A and the pulverized component 13 were added thereto, and they were mixed to become uniform and subsequently cooled.

The resulting mascara had no greasiness, spread well and was easily applied on eyelashes, and made the makeup last much longer.

Example 8

Creamy Eye Shadow

| Components | % by mass |
|---|---|
| 1. Acryl silicone dissolved in D5 (Note 14) | 3.0 |
| 2. Stearyl-modified acryl silicone resin (Note 17) | 2.0 |
| 3. Branched polyether-modified silicone (Note 15) | 1.5 |
| 4. D5 | 25.3 |
| 5. Silicone-modified wax composition B (Preparation Example 2) | 5.0 |
| 6. Dimethyl distearyl ammonium hectorite | 1.2 |
| 7. Hydrophobilized coloring agent (Note 10) | 20.0 |
| 8. Spherical nylon | 3.0 |
| 9. Talc | 4.0 |
| 10. Ethanol | 5.0 |
| 11. Purified water | 30.0 |

(Note 17)
KP-561P supplied from Shin-Etsu Chemical Co., Ltd.

(Production method) The components 1 to 9 were heated and mixed to obtain a uniform dispersion, subsequently a mixture of the components 10 and 11 was added to the dispersion, and they were emulsified to obtain a cream eye shadow.

The resulting cream eye shadow had no oily or powdered feel, spread well and lightly, gave a fresh feel to eyelids and lasted longer.

Example 9

Sun Cut Milky Lotion

| Components | % by mass |
| --- | --- |
| 1. Crosslinked polyether-modified silicone (Note 1) | 3.0 |
| 2. Crosslinked dimethylpolysiloxane (Note 3) | 2.0 |
| 3. Branched polyether-modified silicone (Note 15) | 1.0 |
| 4. Silicone-modified wax composition A (Preparation Example 1) | 6.0 |
| 5. D5 | 4.0 |
| 6. Isotridecyl isononanoate | 4.0 |
| 7. Titanium oxide dispersion (Note 18) | 25.0 |
| 8. Zinc oxide dispersion (Note 19) | 35.0 |
| 9. Dipropylene glycol | 2.0 |
| 10. Sodium citrate | 0.2 |
| 11. Sodium chloride | 1.0 |
| 12. Purified water | 16.8 |

(Note 18)
SPD-T5 supplied from Shin-Etsu Chemical Co., Ltd.
(Note 19)
SPD-Z5 supplied from Shin-Etsu Chemical Co., Ltd.

(Production method) The components 1 to 6 were made into a uniform mixture, then a solution obtained by mixing the components 9 to 12 was added thereto, followed by emulsification. The components 7 and 8 were added to the resulting emulsified mixture to obtain a sun cut milky lotion.

The resulting sun cut milky lotion had no greasy or oily feel, spread well and lightly, gave a fatted film feel to a skin and had a good water resistance on the skin.

Example 10

Sun Cut Cream

| Components | % by mass |
| --- | --- |
| 1. Crosslinked polyether-modified silicone (Note 20) | 3.0 |
| 2. Crosslinked dimethylpolysiloxane (Note 3) | 1.8 |
| 3. Alkyl-modified branched polyether-modified silicone (Note 6) | 1.0 |
| 4. Silicone-modified wax composition F (Preparation Example 6) | 5.0 |
| 5. D5 | 18.0 |
| 6. Octyl methoxycinnamate | 6.0 |
| 7. Acryl silicone resin dissolved product (Note 21) | 10.0 |
| 8. Hydrophobilized fine particle zinc oxide (Note 22) | 20.0 |
| 9. 1,3-Butylene glycol | 2.0 |
| 10. Sodium citrate | 0.2 |
| 11. Sodium chloride | 0.5 |
| 12. Preservative | Adequate quantity |
| 13. Purified water | 32.0 |

(Note 20)
KSG-240 (swollen D5) supplied from Shin-Etsu Chemical Co., Ltd.
(Note 21)
KP-575 supplied from Shin-Etsu Chemical Co., Ltd.
(Note 22)
Treated with AES-3083 supplied from Shin-Etsu Chemical Co., Ltd.

(Production Method)
A: The component 7 was added to a part of the component 5 to obtain a uniform mixture, and the component 8 was added to the mixture, followed by dispersion using a bead mill.
B: The components 1 to 4, 6 and the rest of the component 5 were heated to obtain a uniform mixture, a solution obtained by mixing the components 9 to 13 was added to the mixture, followed by emulsification. Subsequently the dispersion obtained in A was added to the resulting emulsified product to obtain a sun cut cream.

The resulting sun cut cream had no greasy feel, spread well and lightly, and gave a fatted film feel and a non-viscous feel, as well as lasted longer.

Example 11

Lipstick

| Components | % by mass |
| --- | --- |
| 1. Candelilla wax | 4.0 |
| 2. Polyethylene | 2.0 |
| 3. Microcrystalline wax | 3.0 |
| 4. Silicone-modified wax composition D (Preparation Example 4) | 8.5 |
| 5. Stearyl-modified acryl silicone resin (Note 17) | 13.5 |
| 6. Diphenyl dimethicone (Note 23) | 20.0 |
| 7. Acryl silicone dissolved in D5 (Note 14) | 10.0 |
| 8. Alkyl-modified branched polyglycerine-modified silicone (Note 12) | 3.0 |
| 9. Macadamia nut oil | 20.0 |
| 10. Hydrogenated polyisobutene | 10.0 |
| 11. Isotridecyl isononanoate | 6.0 |
| 12. Coloring agent | Adequate quantity |
| 13. Mica | Adequate quantity |

(Note 23)
KF-54 supplied from Shin-Etsu Chemical Co., Ltd.

(Production method) The components 1 to 11 were heated and mixed uniformly, and subsequently the components 12 and 13 were added to the resulting mixture to obtain a uniform mixture, and this mixture was filled in a predetermined container having a high air tightness to obtain a lipstick.

It was confirmed that the resulting lipstick had no greasy or oily feel, no bleeding when given on lips and made the makeup last longer.

Example 12

W/O Liquid Foundation

| Components | % by mass |
| --- | --- |
| 1. Crosslinked polyether-modified silicone (Note 1) | 3.0 |
| 2. Crosslinked dimethylpolysiloxane (Note 3) | 5.0 |
| 3. Branched polyether-modified silicone (Note 15) | 2.0 |
| 4. D5 | 17.0 |
| 5. Silicone-modified wax composition A (Preparation Example 1) | 6.0 |
| 5. Cetyl isooctanoate | 2.0 |
| 6. Polymer A dissolved in D5 | 10.0 |
| 7. Dimethyl distearyl ammonium hectorite | 1.2 |
| 8. Hydrophobilized coloring agent (Note 10) | 14.0 |
| 9. Acryl silicone resin dissolved product (Note 21) | 10.0 |
| 10. 1,3-Butylene glycol | 5.0 |
| 11. Xanthan gum | 0.1 |
| 12. Sodium citrate | 0.2 |
| 13. Sodium chloride | 0.5 |
| 14. Preservative | Adequate quantity |
| 15. Purified water | 24.0 |

(Production Method)

A: A part of the component 4 and the component 9 were mixed, and the component 8 was dispersed in the resulting mixture.

B: A solution obtained by mixing the components 10 to 15 was gradually added to uniform oily mixture obtained by mixing the rest of the component 4, the components 1 to 3 and 5 to 7, followed by emulsification. The dispersion obtained in A was added to the resulting emulsified mixture to obtain a W/O liquid foundation.

The resulting W/O liquid foundation had no greasy or oily feel, spread well and lightly, made the makeup last longer, and scarcely gave a secondary adhesion onto collars and the like.

Example 13

Hair Cream

| Components | % by mass |
| --- | --- |
| 1. Silicone gum dissolved product (Note 24) | 10.0 |
| 2. Trimethylsiloxy silicic acid dissolved in D5 (Note 25) | 10.0 |
| 3. Acryl silicone dissolved in M3T (Note 26) | 10.0 |
| 4. Triethylhexanoin | 5.0 |
| 5. Silicone-modified wax composition A (Preparation Example 1) | 5.0 |
| 6. Stearic acid | 1.5 |
| 7. Cetyl alcohol | 0.5 |
| 8. Polyglyceryl monooleate | 1.5 |
| 9. Glyceryl monostearate | 1.5 |
| 10. Polyether-modified silicone (Note 27) | 0.5 |
| 11. 1,3-Butylene glycol | 5.0 |
| 12. (Acrylates/alkyl acrylate (C10-30)) crosspolymer (Note 28) | 0.3 |
| 13. Triethanolamine | 0.3 |
| 14. Preservative | Adequate quantity |
| 15. Purified water | 48.9 |

(Note 24)
KF-9028 supplied from Shin-Etsu Chemical Co., Ltd.
(Note 25)
KF-7312J supplied from Shin-Etsu Chemical Co., Ltd.
(Note 26)
KP-549 supplied from Shin-Etsu Chemical Co., Ltd.
(Note 27)
KF-6011 supplied from Shin-Etsu Chemical Co., Ltd.
(Note 28)
Pemulen TR-1 supplied from Noveon Inc.

(Production method) The components 1 to 10 were heated and dissolved to form a mixture, and a solution obtained by heating the components 11 to 15 separately was gradually added to the mixture with stirring to thereby effect emulsification, and the resulting emulsified mixture was cooled to obtain a hair cream.

The resulting hair cream spread well and lightly, gave luster and smoothness to hair and exhibited an excellent setting effect on the hair, as well as had water resistance and perspiration resistance, and also lasted longer.

Example 14

O/W Cream

| Components | % by mass |
| --- | --- |
| 1. D5 | 3.0 |
| 2. Stearyl-modified acryl silicone resin (Note 17) | 5.0 |
| 3. Silicone-modified wax composition A (Preparation Example 1) | 15.0 |
| 4. Glycerine triisostearate | 8.0 |
| 5. Cetanol | 1.0 |
| 6. Stearic acid | 3.0 |
| 7. Glycerly monostearate | 1.5 |
| 8. Sorbitan sesquioleate | 0.5 |
| 9. Polyoxyethylene sorbitan monooleate | 1.0 |
| 10. Sodium hydroxide (1% aqueous solution) | 10.0 |
| 11. 1,3-Butylene glycol | 5.0 |
| 12. Preservative | Adequate quantity |
| 13. Purified water | Balance |

(Production method) The components 10 to 14 were heated and dissolved to form a mixture, and a solution obtained by heating the components 1 to 9 separately was added to the mixture to thereby emulsify them, and the emulsified mixture was cooled to obtain an O/W cream.

The resulting O/W cream had no greasy or oily feel, was non-viscous, spread well and lightly, and gave a refreshing feel.

Example 15

O/W Cream

| Components | % by mass |
| --- | --- |
| 1. Methylpolysiloxane (Note 4) | 6.0 |
| 2. Triethylhexanoin | 16.0 |
| 3. Ceresin | 8.0 |
| 4. Crosslinked dimethylpolysiloxane (Note 29) | 8.0 |
| 5. Silicone-modified wax composition A (Preparation Example 1) | 10.0 |
| 6. 1,3-Butylene glycol | 3.0 |
| 7. Branched polyglycerine-modified silicone with a medium HLB (Note 30) | 0.6 |
| 8. Branched polyglycerine-modified silicone with a high HLB (Note 31) | 0.3 |
| 9. Acryl-based thickening agent mixture (Note 32) | 0.6 |
| 10. Sodium chloride (1% aqueous solution) | 8.0 |
| 11. Purified water | 26.5 |
| 12. 5% aqueous solution of acryl-based polymer 2 (Note 33) | 13.0 |

(Note 29)
KSG-16 supplied from Shin-Etsu Chemical Co., Ltd.
(Note 30)
KF-6100 supplied from Shin-Etsu Chemical Co., Ltd.
(Note 31)
KF-6104 supplied from Shin-Etsu Chemical Co., Ltd.
(Note 32)
SIMULGEL 600 supplied from Sepic
(Note 33)
AristoflexAVC supplied from Client (Production method) The components 1 to 5 were heated and dissolved using a hot water bath, and a solution obtained separately by heating the components 6 to 11 was gradually added thereto to thereby emulsify them, and the emulsified mixture was cooled, and then the component 10 was added and mixed to obtain an O/W cream.

The resulting O/W cream had no greasy or oily feel, and gave a fatted film feel as well as a refreshing feel.

Example 16

Comparative Examples 2 and 3

Cream Concealer

|  | Example 16 | Comparative Example 2 | Comparative Example 3 |
|---|---|---|---|
| 1 Ceresin | 5.5 | 5.5 | 5.5 |
| 2 Inulin stearate | — | 2.3 | — |
| 3 Methylpolysiloxane (Note 4) | 2.0 | 11.2 | 13.5 |
| 4 Silicone-modified wax composition A | 11.5 | — | — |
| 5 Cross-linked polyglycerine modified silicone (Note 11) | 4.0 | 4.0 | 4,0 |
| 6 Polymethyl silsesquioxane (Note 8) | 1.5 | 1.5 | 1.5 |
| 7 Neopentyl glycol dioctanoate | 8.0 | 8.0 | 8.0 |
| 8 Triethylhexanoin | 4.0 | 4.0 | 4.0 |
| 9 Alkyl-modified branched polyglycerine modified silicone (Note 12) | 1.5 | 1.5 | 1.5 |
| 10 Hydrophobilized coloring agent (Note 10) | 10.0 | 10.0 | 10.0 |
| 11 Polysorbate 80 | 0.3 | 0.3 | 0.3 |
| 12 Preservative | AQ* | AQ* | AQ* |
| 13 1,3-Butylene glycol | 5.0 | 5.0 | 5.0 |
| 14 Purified water | 46.0 | 46.0 | 46.0 |
| Total (% by mass) | 100.0 | 100.0 | 100.0 |

*"AQ" means "Adequate quantity".

(Production Method)
A: The components 1 to 9 were heated and dissolved to form a uniform mixture.
B: The components 10 to 13 were mixed, dispersed using a roller to form a mixture, then the component 14 was added to the mixture, followed by heating and mixing.
C: While the mixture obtained in A was heated and stirred, the mixture obtained in B was gradually added to the mixture obtained in A to thereby emulsify them, and then the emulsified mixture was cooled with stirring.
D: The emulsified mixture obtained in C was filled in a jar container to obtain a concealer.

In Comparative Example 2, the solid content in the silicone-modified wax composition of Example 16 was replaced with inulin stearate known as being capable of increasing hardness of a wax blended formulation. In Comparative Example 3, the solid content in the silicone-modified wax composition of Example 16 was replaced with methylpolysiloxane. The cream concealer of Example 16 had no greasiness and gave a cosmetic film with thickness, but that of Comparative Example 3 was not viscous and could not form a film with thickness. The cream concealer of Comparative Example 2 could form a film which was thicker than that of Comparative Example 3, but had a low viscosity and gave a poorer a finish than that of Example 16.

INDUSTRIAL APPLICABILITY

The composition of the present invention is easily blended in cosmetic preparations, and gives an adequate viscosity to the cosmetic preparations. The composition can be combined with other thickening agents to form a cosmetic preparation which is good in stability with time and temperature stability. The cosmetic preparation gives a refreshing feel with no greasiness and forms a fatted cosmetic film.

What is claimed is:

1. A composition for a cosmetic preparation, comprising a silicone-modified olefin wax having a melting point of 100° C. or above and an unctuous agent having a melting point of 80° C. or below, wherein the composition is prepared by cooling after dissolving and mixing the silicone-modified olefin wax and the unctuous agent at a temperature equal to or higher than the melting point of the silicone-modified olefin wax,
   wherein the silicone-modified olefin wax is a copolymer obtained by adding an organohydrogenpolysiloxane to a copolymer obtained by copolymerizing ethylene, at least one olefin being selected from $\alpha$-olefins having 3 to 12 carbon atoms and vinyl norbornene.

2. The composition according to claim 1, wherein the silicone-modified olefin wax is contained in an amount of 10 to 40% by mass and the unctuous agent is contained in an amount of 90 to 60% by mass based on the total mass of the composition.

3. The composition according to claim 1, wherein the silicone-modified olefin wax is a butylpolydimethylsiloxyl (ethylene/propylene/vinyl norbornene) copolymer.

4. The composition according to any one of claims 1, 2 and 3, wherein the melting point of the unctuous agent is 30° C. or below.

5. The composition according to any one of claims 1, 2 and 3, wherein the composition is in a paste or slurry form at room temperature.

6. A cosmetic preparation comprising a composition according to any one of claims 1, 2 and 3.

7. The cosmetic preparation according to claim 6, further comprising at least one wax selected from the group consisting of hydrocarbon-based waxes and natural waxes.

8. A method of preparing a composition for a cosmetic preparation, comprising:
   1) a step of dissolving and mixing a silicone-modified wax having a melting point of 100° C. or above and an unctuous agent having a melting point of 80° C. or below at a temperature equal to or higher than the melting point of the silicone-modified wax, and
   2) a step of cooling a mixture obtained in step 1) with stirring.

9. A method of preparing a preparation, comprising:
1) a step of dissolving and mixing a silicone-modified wax having a melting point of 100° C. or above and an unctuous agent having a melting point of 80° C. or below at a temperature equal to or higher than the melting point of the silicone-modified wax,
2) a step of cooling a mixture obtained in the step 1) with stirring, and
3) a step of mixing a composition obtained in the step 2) with at least one component of other components to be blended in the cosmetic preparation at a temperature lower than 100° C.

10. The method according to claim 9, wherein the at least one component in the step 3) is at least one wax selected from hydrocarbon-based waxes and natural waxes, said method further comprising 4) a step of cooling a mixture obtained in the step 3) with stirring.

11. The method according to claim 8, wherein the silicone-modified wax is contained in an amount of 10 to 40% by mass and the unctuous agent is contained in an amount of 90 to 60% by mass based on the total mass of the composition.

12. The method according to claim 8, wherein the silicone-modified wax is a silicone-modified olefin wax.

13. The method according to claim 12, wherein the silicone-modified olefin wax is a copolymer obtained by adding an organohydrogenpolysiloxane to a copolymer obtained by copolymerizing ethylene, at least one olefin selected from α-olefins having 3 to 12 carbon atoms and vinyl norbornene.

14. The method according to claim 13, wherein the silicone-modified olefin wax is a butylpolydimethylsiloxyl (ethylene/propylene/vinyl norbornene) copolymer.

15. The method according to claim 8, wherein the melting point of the unctuous agent is 30° C. or below.

16. The method according to claim 8, wherein the unctuous agent having a melting point of 80° C. or below is a silicone oil.

17. The method according to claim 9, wherein the silicone-modified wax is contained in an amount of 10 to 40% by mass and the unctuous agent is contained in an amount of 90 to 60% by mass based on the total mass of the composition.

18. The method according to claim 9, wherein the silicone-modified wax is a silicone-modified olefin wax.

19. The method according to claim 18, wherein the silicone-modified olefin wax is a copolymer obtained by adding an organohydrogenpolysiloxane to a copolymer obtained by copolymerizing ethylene, at least one olefin selected from α-olefins having 3 to 12 carbon atoms and vinyl norbornene.

20. The method according to claim 19, wherein the silicone-modified olefin wax is a butylpolydimethylsiloxyl (ethylene/propylene/vinyl norbornene) copolymer.

21. The method according to claim 9, wherein the melting point of the unctuous agent is 30° C. or below.

22. The method according to claim 9, wherein the unctuous agent having a melting point of 80° C. or below is a silicone oil.

* * * * *